United States Patent [19]

Neirinckx

[11] 4,419,339
[45] Dec. 6, 1983

[54] FORMULATION AND METHOD OF MAKING CATIONIC LIPOPHILIC COMPLEXES

[75] Inventor: Rudi D. Neirinckx, East Windsor, N.J.

[73] Assignee: E. R. Squibb & Sons, Inc., Princeton, N.J.

[21] Appl. No.: 290,268

[22] Filed: Aug. 5, 1981

[51] Int. Cl.$^3$ .................... A61K 43/00; A61K 49/00; C07F 15/02; C07F 1/08
[52] U.S. Cl. .............................. 424/1.1; 260/429 R; 260/429 J; 260/438.1; 260/439 R; 424/9
[58] Field of Search .................. 424/1, 9; 260/429 R, 260/429 J, 438.1, 439 R

[56] References Cited

U.S. PATENT DOCUMENTS 4,374,821  2/1983  Glavan et al. ................. 260/429 R

OTHER PUBLICATIONS

Deutsch et al., Chem. Abstracts, vol. 96 (1982) #168787t.
Deutsch et al., J. Nucl. Med., 22:897–907 (1981).
Spitznagle et al., J. Nucl. Med., 22: P13 (1981).
J. Nucl. Med., 21 (6): p. P56 (1980).
J. Nucl. Med., 22 (6): p. P51 (1981).
Nature, 1959, pp. 1039–1040.
J. Chem. Soc. (London), 1950, pp. 851–856.

*Primary Examiner*—Christine M. Nucker
*Attorney, Agent, or Firm*—Lawrence S. Levinson; Donald J. Barrack

[57] ABSTRACT

A method for the preparation of a technetium-99m complex having the formula $$[(L)_2{}^{99m}Tc(X)_2]^{\oplus} X^{\ominus},$$

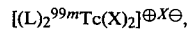

which comprises adding technetium-99m to a complex having the formula $$[(L)_2 M(X)_2]^{\oplus} X^{\ominus}$$

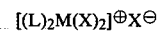

and heating the mixture in the presence of a source of anion $X^{\ominus}$, wherein each L is the same or different lipophilic ligand, each X is the same or different monovalent anionic ligand, and M is a non-toxic trivalent metal ion, is disclosed.

20 Claims, No Drawings

FORMULATION AND METHOD OF MAKING CATIONIC LIPOPHILIC COMPLEXES

BACKGROUND OF THE INVENTION

Deutsch and Glavan have prepared cationic lipophilic complexes of technetium-99m that are useful as negative heart imaging agents. The agents that they have prepared accumulate in the normal heart and visualize an infarct as a cold area on a relatively hot background of normal tissue.

The expression "cationic lipophilic complexes of technetium-99m" is used by Detusch and Glavan to describe complexes of technetium-99m having lipophilic ligands and an overall cationic charge. Their preferred complexes are described by the formula $$[(L)_2{}^{99m}Tc(X)_2]^{\oplus}X^{\ominus}, \qquad I$$

wherein each L represents the same or different lipophilic ligand strongly chelating for a technetium-99m cation, and wherein the three X's are the same or different monovalent anionic ligand.

The above-described complexes are prepared by Deutsch and Glavan using the following procedure. The ligand and technetium-99m (in the form of pertechnetate ion or reduced derivative thereof) are first complexed in a mono- or biphasic system. A large (preferably greater than ten fold) excess of lipophilic ligand over technetium is used. The resulting complex is isolated and purified using standard chromatographic techniques. Finally, the "purified" complex is dissolved (or suspended) in a pharmacologically acceptable administration vehicle. Among the vehicles suggested by Deutsch and Glavan are saline, 50/50 ethanol/saline, vehicles wherein the concentration of ethanol is varied, vehicles wherein ethanol is replaced by other organic portions such as propylene glycol, glycerol or dimethyl sulfoxide, or vehicles based on solubilization of the radiopharmaceutical in micelles.

BRIEF DESCRIPTION OF THE INVENTION

The work of Deutsch and Glavan described above is a major step forward in the search for a technetium-99m agent that can be used for myocardial imaging. However, the multi-step methodology used by Deutsch and Glavan is not practical for routine use in a clinical environment due mainly to the required chromatographic purification procedure.

It is recognized by Deutsch and Glavan that their procedure for preparing [$^{99m}$Tc(DMPE)$_2$Cl$_2$]$^{\oplus}$ yields the desired material in combination with various impurities, predominantly the corresponding neutral material. Their chromatographic purification procedure yields, however, a product that is still substantially contaminated with another more hydrophilic cation; the cation does not localize in the myocardium.

It is an object of this invention to provide formulations and methodology acceptable for use in a clinical environment for synthesizing cationic lipophilic complexes of technetium-99m.

The methodology of this invention comprises the preparation of a complex having the formula $$[L_2{}^{99m}Tc(X)_2]^{\oplus}X^{\ominus}, \qquad I$$

by the reaction of technetium-99m with a complex having the formula $$[(L)_2M(X)_2]^{\oplus}X^{\ominus}, \qquad II$$

in the presence of a source of anion ($X^{\ominus}$). In formulas I and II, and throughout the specification the symbols are as defined below.

Each L represents the same or different lipophilic ligand (preferably the lipophilic ligands in each of formulas I and II are the same);

Each X represents the same or different monovalent anionic ligand (preferably the anionic ligands which are part of the cationic lipophilic complex are the same, and most preferably all three monovalent anionic ligands in each of formulas I and II are the same); and M is any trivalent metal that is non-toxic and able to form a solid [(L)$_2$M(X)$_2$]$^{\oplus}$ complex which can be decomposed under conditions whereby the corresponding technetium-99m complex can be formed. Exemplary metals are the trivalent metals from the first and second rows of the transition elements in the periodic table and the trivalent lanthanides. M is preferably a trivalent metal ion selected from the first row of the transition elements, and is most preferably iron.

The formulation of this invention comprises a complex of formula II in combination with a source of anion $X^{\ominus}$. A chelating agent may, optionally, also be present.

DETAILED DESCRIPTION OF THE INVENTION

Cationic lipophilic complexes of technetium-99m having the formula $$[(L)_2{}^{99m}Tc(X_2)]^{\oplus}X^{\ominus} \qquad I$$

are useful for measuring myocardial perfusion and the diagnosis of ischemia and infarction.

In formula I, the preferred lipophilic ligands (L) can be described by the general formula $$[A-(Y:)_n \qquad III$$

wherein n is 2, 3, 4 or 5 (preferably 2 or 3) and wherein A represents an alkylene lipophilic radical, or a monocyclic or polycyclic cycloaliphatic or aromatic lipophilic radical which may optionally be heterocyclic by containing in the ring or rings thereof, an atom selected from the group consisting of N, O, P, S, or B. Most preferably, A is a lower alkylene radical, or A is a monocyclic or polycyclic aromatic radical. A may further be substituted, when necessary to increase the hydrophilic character of the molecule, with water solubilizing neutral groups such as hydroxy groups, thiol groups, carbonyl groups, and the like. Y: is a neutral functional group having a free electron pair, capable of complexing with a Tc-99m cation having oxidation states less than +VII, preferably ranging from +I to +V. Thus, Y: may either be $Y^1R_2$ or $Y^2R$. $Y^1$ may be selected from the group consisting of N, P, As, Sb, or Bi. $Y^2$ can be selected from the group consisting of O, S, Se or Te. R is hydrogen or a $C_1$-$C_{15}$ straight or branched chain alkyl group. R may be unsubstituted or be substituted along the hydrocarbon chain with oxygens, nitrogen, sulfurs, or phosphorus, to thereby control the lipophilicity of the technetium-99m complex.

Exemplary lipophilic ligands (L) are the following: (CH$_3$)$_2$P-CH$_2$CH$_2$-P(CH$_3$)$_2$, bis (1,2-dimethylphosphino)ethane, also known as "DMPE";

o-C6H4(As(CH3)2)2, o-phenylene bis(dimethylarsine), also known as "DIARS";

(C6H5)2P-CH2CH2-P(C6H5)2, bis(1,2-diphenylphosphino)ethane, also known as "diphos";

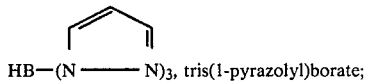
HB—(N———N)3, tris(1-pyrazolyl)borate;

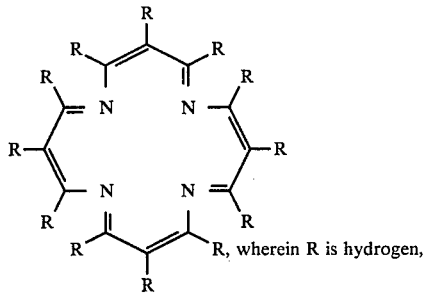
wherein R is hydrogen, alkyl (preferably methyl or ethyl), phenyl or hydroxy, porphyrins;

P(CH2CH2P(C6H5)2)3, tris[2-(diphenylphosphino)ethyl]phosphine, also known as "tetraphos";

(C6H5)2AsCH2CH2As(C6H5)2, 1,2-bis(diphenylarsino)ethane, also known as "DAE";

NH2CH2CH2NHCH2CH2NH2, di(ethylamine)amine, also known as "DIEN";

(RN(CH2CH2P(C6H5)2), wherein R is hydrogen, $C_1$-$C_{15}$ alkyl, or $C_1$-$C_{15}$ alkyl substituted by polar functional groups capable of rendering the resulting radical R with a wide range of hydrophilicity. A preferred series of radicals R are those described in: Nuzzi et al, J. Amer. Chem. Soc., 101 3683(1979) and Wilson et al, ibid, 100, 2269(1978), the disclosures of which are incorporated herein by reference;

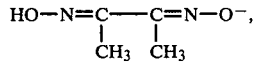
dimethylglyoxime, also known as "DMG";

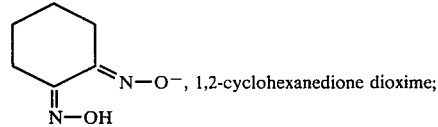
1,2-cyclohexanedione dioxime;

H2PCH2CH2PH2, 1,2-bis(dihydrophosphino)ethane;
H2NCH2CH2SH, 2-aminoethanethiol, also known as "cysteamine";
H2AsCH2CH2AsH2, 1,2-bis(dihydroarsino)ethane;
H2NCH2CH2NH2, ethylenediamine;
(CH3)2NCH2CH2N(CH3)2, 1,2-bis(dimethylamino)ethane;

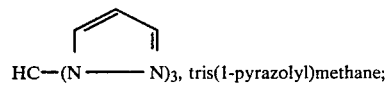
HC—(N———N)3, tris(1-pyrazolyl)methane;

o-C6H4(P(CH3)2)2, o-phenylene bis(dimethylphosphine);
o-C6H4(PH2)2, o-phenylene bis(dihydrophosphine);
o-C6H4(N(CH3)2)2, o-phenylene bis(dimethylamine);
o-C6H4(NH2)2, o-phenylene diamine;
o-C6H4((AsH2))2, o-phenylene bis (dihydroarsine, and
(CH3)2AsCH2CH2As(CH3)2, 1,2-bis(dimethylarsino)ethane.

The above lipophilic ligands (L) are exemplary. It should be emphasized that any ligand which would render the technetium complex of formula I lipophilic may be used. The preferred ligands (L) are DMPE and DIARS.

The metal complexes of formula II can be prepared using art recognized procedures; see, for example, R. S. Nyholm, J. Chem. Soc., 851–856(1950). As described therein, [Fe(diars)2Cl2]$\oplus$FeCl4$\ominus$ can be prepared by mixing a solution of 1.7 g of ferric chloride in 75 ml of ethanol or benzene with a solution of 2.9 g of o-phenylenebisdimethylarsine in 80 ml of ethanol or benzene, and filtering the resulting precipitate. Additional details on the preparation of the complexes of formula II are noted in the examples. This methodology is readily adaptable to use in the preparation of other complexes of formula II.

The preparation of a technetium-99m complex of formula I is accomplished by adding technetium-99m to a solid complex of formula II in the presence of anion (X$\ominus$) and heating the mixture. If the metal (M) is not soluble in the reaction medium it may be necessary to add a complexing agent to maintain the metal in solution during heating. It may also be desirable to add a solubilizing agent for the ligand (L). During the ligand exchange reaction, the solubilizing agent prevents volatilization of the ligand.

Anion (X$\ominus$) is present when the technetium-99m is added to the complex of formula II. Most conveniently, the anion (in the form of a salt) will be formulated with the solid complex of formula II and additional adjuvants (if any). Exemplary anions are the halogens, chloride being most preferred; any other pharmaceutically acceptable anion is, however, also acceptable.

Technetium-99m is available as a product from commercial sources such as manufacturing companies and radiopharmacies. Because of the relatively short half-life of technetium-99m it is most desirable to generate the radionuclide as close to its time of use as possible. The most common source of technetium-99m is the parent-daughter generator. Molybdenum-99 (the "parent" radionuclide) is maintained on a containerized support medium (usually alumina) and, when eluted with the proper eluant (usually saline) technetium-99m in the form of pertechnetate ion ($^{99m}TcO_4^\ominus$) is generated; see, for example, U.S. Pat. Nos. 3,369,121 and 3,920,995.

Various complexing (also known in the art as chelating) agents can be used in the process of this invention. The complexing agent should be pharmaceutically acceptable and able to keep M in solution after the decomposition of complex II. Exemplary complexing agents are ethylene glycol-bis($\beta$-aminoethyl ether)-N,N'-tetraacetic acid (EGTA), ascorbic acid, sulfosalicyclic acid, and other complexing agents that will not interfere with the synthesis of complex I at an acceptable pH (2–7).

The particular reaction conditions needed for the ligand exchange reaction of this invention will depend on the particular complex of formula II being used. In general, however, the reaction will be run at a temperature of about 30° to 180° C., preferably about 30° to 130° C.

After the ligand exchange reaction is complete water can (optionally) be added to the reaction mixture. The water may be desirable to reduce the saline concentration of the preparation to isotonicity with blood.

The complexes of formula II exist as stable solid salts that can be conveniently formulated by manufacturers to allow for a minimum number of manipulative steps by the medical technicians responsible for the preparation of cationic lipophilic complexes of technetium-99m (formula I). The most advantageous formulation comprises a metal complex of formula II and a source of anion. As discussed above, it may also be desirable to include a complexing agent in the formulation. The concentration of anion is not critical, but it does govern the rate of the ligand exchange reaction; preferably the anion will be present in an amount sufficient to provide a concentration of 0.5 molar after the technetium-99m has been added. The molar ratio of metal complex/complexing agent is also not critical and can be between about 10:1 and 1:10.

The formulation can also contain various adjuvants. Preservatives, such as alkyl parabens (e.g., methyl paraben and propyl paraben), and solubilizing agents for the ligand L (e.g., PVP, ethylene glycol distearate, glycol and phenyl salicyclic acid. Salts of calcium and magnesium may also be present to "neutralize" any undesirable effects in the body of excess complexing agent which may be present.

The following examples are specific embodiments of this invention.

EXAMPLE 1

[[bis(1,2-dimethylphosphino)ethane]$_2$Fe(Cl)$_2$]$^\oplus$Cl$^\ominus$

Ferric chloride (3.60 g) and anhydrous methanol (350 ml) are placed in a 500 ml 3-necked round bottom flask equipped with condenser, inlet-outlet tubes and Teflon®-coated stir bar. The apparatus is flushed with nitrogen for 15 minutes, followed by the addition of 5 g of bis(1,2-dimethylphosphino)ethane. The mixture is stirred and heated at 60°–65° C. for 2 hours, and the resulting solution is allowed to cool at room temperature and stir for an additional 14 hours. The solution is filtered and the filtrate is concentrated, under vacuum, to approximately 150 ml. Ethyl ether is added to the concentrated solution causing the title compound to precipitate. The product is filtered and washed with ethyl ether, yielding 8.85 g of material.

EXAMPLE 2

[[bis(1,2-dimethylphosphino)ethane]$_2$$^{99m}$Tc(Cl)$_2$]$^\oplus$Cl$^\ominus$

Method I

[[bis(1,2-Dimethylphosphino)ethane]$_2$Fe(Cl)$_2$]$^\oplus$Cl$^\ominus$ (4 mg), ethylene glycol-bis[β-aminoethyl ether]-N,N'-tetraacetic acid (1.6 mg) methyl paraben (1.8 mg), propyl paraben (0.2 mg), calcium chloride (0.64 mg) and sodium chloride (29 mg) are added to a 5 ml glass vial. A 0.9% saline solution of pertechnetate ion is added to the vial and the mixture is heated for 45 minutes at 125° C. Analysis by high pressure liquid chromatography shows that greater than 99% of the $^{99m}$Tc is the form of [[bis(1,2-dimethylphosphino)ethane]$_2$$^{99m}$Tc(Cl)$_2$]$^\oplus$Cl$^\ominus$.

Method II

[[bis(1,2-Dimethylphosphino)ethane]$_2$Fe(Cl)$_2$]$^\oplus$Cl$^\ominus$ (5 mg) and sodium chloride (21 mg) are added to a 5 ml glass vial. A 7.5% ethanol solution and a 0.9% sodium chloride solution of pertechnetate ion is added and the mixture is heated for 45 minutes at 125° C. Analysis by high pressure liquid chromatography shows that greater than 99.5% of the $^{99m}$Tc is in the form of [[bis(1,2-dimethylphosphino)ethane]$_2$$^{99m}$Tc)Cl)$_2$]$^\oplus$Cl$^\ominus$.

What is claimed is:

1. A method for the preparation of a technetium-99m complex having the formula $$[(L)_2{}^{99m}Tc(X)_2]^\oplus X^\ominus,$$

which comprises adding technetium-99m to a complex having the formula $$[(L)_2M(X)_2]^\oplus X^\ominus$$

and heating the mixture in the presence of a source of anion $X^\ominus$, wherein each L is the same or different lipophilic ligand, each X is the same or different monovalent anionic ligand, and M is a non-toxic trivalent metal ion other than technetium.

2. A method in accordance with claim 1 additionally comprising the step of adding water, after the reaction has been completed.

3. A method in accordance with claim 1 wherein the technetium-99m is added in the form of a saline solution of pertechnetate ion.

4. A method in accordance with claim 1 wherein M is iron.

5. A method in accordance with claim 1 wherein a complexing agent is present during the heating of the mixture.

6. A method in accordance with claim 1 for the preparation of [[bis(1,2-dimethylphosphino)ethane]$_2$$^{99m}$Tc(Cl)$_2$]$^\oplus$Cl$^\ominus$ which comprises the addition of a saline solution of pertechnetate ion to [[bis(1,2-dimethylphosphino)ethane]$_2$Fe(Cl)$_2$]$^\oplus$Cl$^\ominus$ and heating the mixture in the presence of a source of chloride ion and a complexing agent.

7. A method in accordance with claim 6 wherein the source of chloride ion is sodium chloride and the complexing agent is ethylene glycol-bis[β-aminoethyl ether]-N,N'-tetraacetic acid.

8. A composition comprising a complex having the formula $$[(L)_2M(X)_2]^\oplus X^\ominus,$$

wherein each L is the same or different lipophilic ligand, each X is the same or different monovalent anionic ligand, and M is a non-toxic trivalent metal ion other than technetium, and a source of anion $X^\ominus$.

9. A composition in accordance with claim 8 wherein M is iron.

10. A composition in accordance with claim 8 wherein each L is bis(1,2-dimethylphosphino)ethane.

11. A composition in accordance with claim 8 wherein each L is o-phenylene bis(dimethylarsine).

12. A composition in accordance with claim 8 wherein the source of anion $X^\ominus$ is a chloride salt.

13. A composition in accordance with claim 8 additionally containing a complexing agent.

14. A composition in accordance with claim 8 comprising [[bis(1,2-dimethylphosphino)ethane]$_2$Fe(Cl)$_2$]$^\oplus$Cl$^\ominus$ and a source of chloride ion.

15. A composition in accordance with claim 8 additionally comprising one, or more, alkyl paraben.

16. A composition in accordance with claim 8 additionally comprising a calcium or magnesium salt.

17. A composition in accordance with claim 8 additionally comprising calcium chloride.

18. A composition in accordance with claim 14 additionally containing ethylene glycol-bis[β-aminoethyl ether]-N,N'-tetraacetic acid.

19. A composition in accordance with claim 14 wherein the source of chloride ion is sodium chloride.

20. [[bis(1,2-dimethylphosphino)ethane]$_2$Fe(Cl)$_2$]$^{\oplus}$ Cl$^{\ominus}$.